United States Patent [19]

Settle et al.

[11] 4,013,068
[45] Mar. 22, 1977

[54] ELECTROENCEPHALOGRAPHIC ACTIVATED CONTROL SYSTEM

[76] Inventors: Wayne L. Settle, 1311 33rd Ave.; Lowell G. Funston, 1309 33rd Ave., both of San Francisco, Calif. 94122

[22] Filed: Oct. 15, 1974

[21] Appl. No.: 514,539

[52] U.S. Cl. .................. 128/2.1 B; 128/419 R; 340/279; 340/407
[51] Int. Cl.$^2$ .................................. A61B 5/04
[58] Field of Search .......... 128/2.1 A, 2.1 B, 2.1 R, 128/2.05 T, 2.06 F, 419 R; 340/407, 279

[56] References Cited

UNITED STATES PATENTS

| | | | |
|---|---|---|---|
| 3,717,140 | 2/1973 | Greenwood | 128/2.05 T |
| 3,753,433 | 8/1973 | Bakerich et al. | 128/2.1 B |
| 3,760,796 | 9/1973 | Baessler | 128/2.1 B |
| 3,774,593 | 11/1973 | Hakata et al. | 128/2.1 B |
| 3,858,574 | 1/1975 | Page | 128/2.05 T |

OTHER PUBLICATIONS

Dewan, "Nature" vol. 214, June 3, 1967, pp. 975–977.

Primary Examiner—William E. Kamm
Attorney, Agent, or Firm—Townsend and Townsend

[57] ABSTRACT

An EEG activated conrol system responsive to voluntarily or consciously produced EEG signals encoded to correspond to a plurality of commands. There is provided an EEG sensor, typically including electrodes to be worn by the subject and suitable amplification, filtering and pulse-forming circuitry to isolate a desired frequency band of EEG signals and produce pulse signals corresponding thereto. The pulse signals, representative of the EEG signals, from the sensor are applied to command decoder circuitry adapted to detect and differentiate the encoded signals corresponding to the desired command. Suitable actuators are provided to accomplish the desired physical results in response to the decoded commands. A visual display or other feedback device may also be provided to enable the subject to determine that he has successfully produced the encoded EEG signal corresponding to the desired command. In accordance with the preferred embodiment, the particular EEG signals employed comprise the alpha waves and the encoding system comprises a serial digital technique wherein each command comprises a specific number of alpha waves in a burst of alpha activity.

18 Claims, 4 Drawing Figures

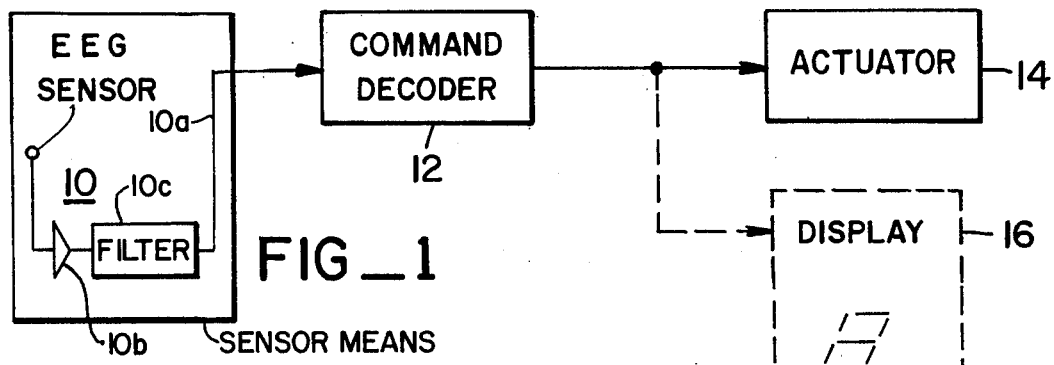
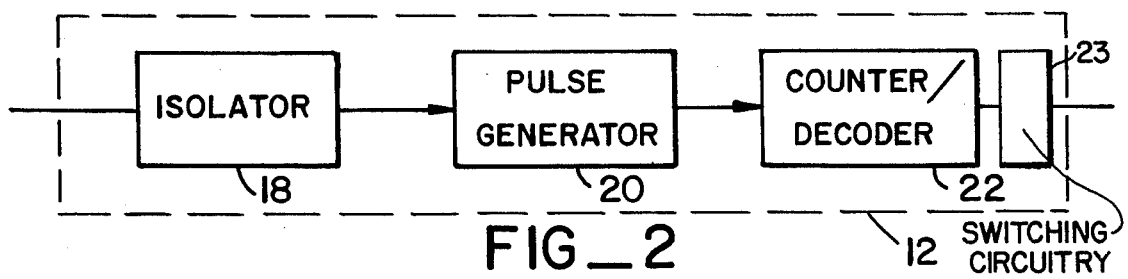
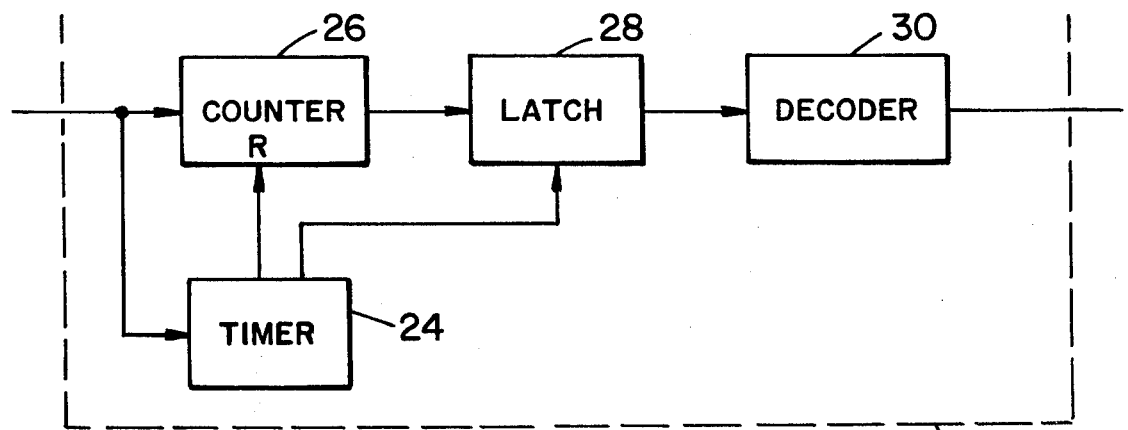
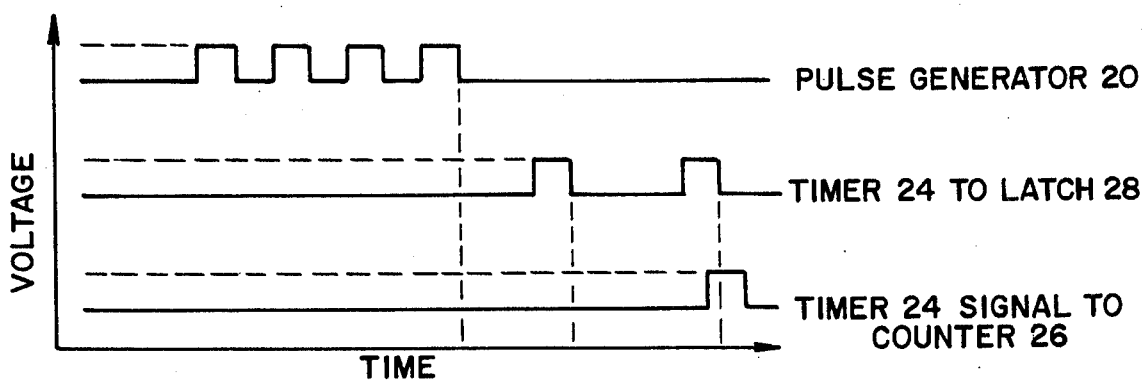

ELECTROENCEPHALOGRAPHIC ACTIVATED CONTROL SYSTEM

This invention relates to control systems responsive to electroencephalographic (hereinafter referred to as EEG) activity, and more particularly, to an EEG activated control system responsive to voluntarily generated encoded EEG signals.

For many years biological activities of the human body have been electrically detected and measured and/or displayed, primarily as an aid to the physician in the detection of disease. With respect to "brain waves" or EEG signals, physicians have employed electroencephalograms of the electrical activity of the brain as a useful, if somewhat crude, indicator of the cerebral processes occurring in humans. For the most part, it has been assumed that EEG activity is primarily not voluntarily controllable. Thus, while there have been attempts to employ EEG activity to control external electrical or electro-mechanical systems, these attempts generally were not adapted to respond to voluntary or conscious efforts of the subject to control his EEG activity. Typical of such attempts are U.S. Pat. Nos. 2,690,178 and 3,032,029. In the former, EEG activity is monitored to automatically control the administration of drugs to a patient while in the latter EEG activity is monitored to control systems for stimulating the subject into an alert state when brain activity indicates the absence of such a state. In essence, these and other prior art systems were adapted to monitor involuntary EEG activity and were not adapted or intended to respond to voluntarily produced EEG "commands" by the subject.

In recent years, EEG feedback systems have been developed which enable the subject to learn to consciously control his own EEG activity. Generally, these systems convert EEG activity to audible tones as exemplified by U.S. Pat. No. 3,753,433. Most commonly, such feedback systems are employed to teach the subject to produce a particular range of frequencies of EEG activity, commonly known as alpha waves, and thereby enable the subjects to achieve the beneficial physiological effects accompanying such EEG activity, commonly referred to as the alpha state, on demand.

In accordance with the present invention, there is provided an EEG activated control system responsive to voluntarily or consciously produced EEG signals. Preferably, EEG signals are voluntarily or consciously encoded to correspond to a plurality of commands and suitable apparatus is provided to decode or differentiate the signals and activate associated electrical or electromechanical apparatus adapted to achieve the desired result. To this end, the apparatus of the present invention generally comprises an EEG sensor, typically including electrodes to be worn by the subject and suitable amplification, filtering and pulse-forming circuitry to isolate a desired frequency band of EEG signals and produce pulse signals corresponding thereto. The pulse signals, representative of the EEg signals, from the sensor are applied to command decoder circuitry adapted to detect and differentiate the encoded signals corresponding to the desired command. Suitable actuators are provided to accomplish the desired physical results in response to the encoded commands. A visual display or other feedback device may also be provided responsive to the command decoder circuitry to enable the subject to determine that he has successfully produced the encoded EEG signal corresponding to the desired command.

In accordance with the preferred embodiment of the present invention, the particular EEG signals employed comprise the alpha waves generally falling within the frequency range from 7.5 to 13 Hz. The preferred encoding system comprises a serial digital technique wherein each command comprises a specific number of alpha waves in a burst of alpha activity. Thus, one command might comprise a burst of alpha activity of two alpha waves in duration whereas another command might comprise a burst of three alpha waves. The bursts of alpha signals are produced by the subject's voluntary entry into the alpha state for the appropriate duration. Thus, the command decoder circuitry according to the preferred embodiment comprises a counter for the sensed alpha waves of a burst of alpha signal and suitable circuitry to register the corresponding command upon cessation of the alpha burst. Preferably timing circuitry requiring the alpha waves to be received within a specified time is provided, to render the apparatus unresponsive to randomly occurring alpha signals involuntarily produced by the subject.

The EEG activated control system according to the present invention thus enables control of electrical or electro-mechanical apparatus through voluntary control of brain wave patterns and without any physical activity on the part of the subject. Thus, the system of the present invention is particularly adapted for use by subjects having impairments preventing physical activation of the apparatus to be controlled. An exemplary application would be the EEG activated control of an electro-mechanical wheelchair by a subject suffering from a paralysis which renders the physical control of the wheelchair difficult or impossible. In this exemplary application, the encoded commands might correspond to commands to the various motors of the wheelchair to cause the wheelchair to stop-go, reverse, turn right and/or left. According to the preferred embodiment of the present invention these commands would typically correspond to alpha bursts of two through five alpha waves, respectively.

It is thus apparent that the present invention achieves what may be referred to as "mental control" of physical apparatus in a simple and efficient manner. The electronic circuitry of the present invention is neither complex nor expensive and may thus achieve wide application as an aid to both the physically impaired as well as unimpaired subjects. While some training may be required to enable the subject to produce the desired EEG signal at will, such result has already been achieved by the applicants and the capability of similar voluntary EEG control by others is reflected in the literature. Thus, the training required to practice the necessary mental control according to the present invention should not impose any great obstacle to the application of the present invention.

These and other objects, features and advantages of the present invention will be more readily apparent from a detailed description wherein reference is made to the accompanying drawings in which:

FIG. 1 is an electrical block diagram of the EEG activated control system of the present invention;

FIG. 2 is a detailed block diagram of the command decoder portion of the apparatus of FIG. 1;

FIG. 3 is a more detailed block diagram of the counter/decoder portion of the apparatus of FIG. 2;

FIG. 4 is a graph depicting the electrical timing of the apparatus of FIG. 3.

Referring initially to FIG. 1, the electroencephalographic activated control system of the present invention generally comprises an EEG sensor means 10 which detects and processes the EEG signals for transmission to a command decoder 12. Command decoder 12 generally comprises suitable circuitry to detect and differentiate the encoded command information, if any, present on the signals from the EEG sensor. The commands thus decoded are applied to suitable electrical or electro-mechanical actuators 14 which are adapted to accomplish the desired results corresponding to the specific commands. A visual display 16 or other feedback device may also be provided responsive to the command decoder 12 to display to the subject a representation, typically numeric, of the decoded commands, to enable the subject to determine that he has successfully produced the encoded EEG signals corresponding to the desired command.

In greater detail, EEG sensor means 10 is of the conventional type typically employed in modern bio-feedback apparatus. Thus, the EEG sensor 10 includes a plurality of electrodes or EEG sensors 10a to be worn by the subject and suitable amplification 10b, filtering 10c and pulse-forming circuitry to isolate and amplify a desired frequency band of EEG signals, and produce pulse signals corresponding thereto. Suitable apparatus is depicted in the January 1973 edition of *Popular Electronics* magazine at pages 40–45. The pulse-forming circuitry typically comprises a monostable multivibrator so that the EEG Sensor means 10 will produce a relatively uniform pulse for each detected EEG wave within the desired frequency band.

In accordance with the preferred embodiment of the present invention the particular frequency range of EEG signals employed comprises the alpha waves generally falling within the frequency range from 7.5 to 13 Hz. This frequency range is employed as applicants have found that the voluntary production of these frequency EEG signals is relatively easy to learn.

The nature of the actuators 14 is determined, in large part, by the desired application of the EEG activated control system of the present invention. In general, actuators 14 may comprise any electrical or electro-mechanical circuitry which may be energized by a signal from command decoder 12. Typical of such devices are transistor switching circuits, relays, electromechanical actuators and the like. Of course, the simplicity or complexity of the actuators 14 depends upon the particular results to be achieved in response to the commands.

Display 16 is optional, and is thus depicted in dashed outline in FIG. 1. Display 16 functions to provide feedback to the subject indicating the command decoded, and any suitable apparatus which may achieve this result can be employed. In accordance with the preferred embodiment of the present invention, each command is represented by a number digit, and thus display 16 preferably comprises a visual digital display. Such a display may be readily provided in the form of a conventional seven segment numeric indicator with suitable driver circuitry. As will be described in greater detail hereinafter, the encoded commands are preferably decoded into binary coded decimal (BCD) signals in the command decoder 12 in accordance with the preferred embodiment of the present invention. Thus, the driver circuitry associated with the preferred seven segment display 16 need merely comprise a BCD to seven segment decoder/driver such as the type 7447 integrated circuit available at Radio Shack stores.

The structure of command decoder 12 is determined, in large part, by the particular encoding system to be employed. While a variety of encoding techniques may be employed, the preferred encoding system according to the present invention comprises a specific number, in excess of one, of sequential alpha waves in a burst of alpha activity. Thus, one command might comprise a sequence of two alpha waves whereas another command might comprise a sequence of three waves. The bursts of alpha waves are produced by the subject's voluntary entry into the alpha state for an appropriately short time interval. Accordingly, the EEG activated control system according to the preferred embodiment of the present invention is generally insensitive to variations in the amplitude and/or frequency of the EEG signals, so long as the signals are within the desired frequency range and are of sufficient magnitude above a threshold level to be readily differentiated from background noise.

Referring now to FIG. 2, command decoder 12 according to the preferred embodiment of the present invention comprises an isolator or data link 18 to which the pulses representative of the sensed EEG signals are applied. Isolator 18 functions primarily to transmit the signals to the logic circuitry of the command decoder 12 while maintaining electrical isolation between the EEG sensor 10 and the remainder of the apparatus. Each electrical isolation constitutes a safety feature to prevent the application of possibly dangerous electrical signals via the EEG sensor 10 in the event of a malfunction downstream of the isolator 18. Accordingly, isolator 18 is not essential to the operation of the present invention and may be regarded simply as a means for transmitting the sensed EEG signals to the downstream logic circuitry. Since the signals from EEG sensor 10 are preferably pulses of uniform amplitude, the isolator or data link 18 may be a relatively simple or low signal quality device. Isolator 18 may typically comprise a conventional solid state optical isolator, such as the Hewlett Packard 4351 optical isolator, to provide the desired electrical isolation. Alternatively, it is likely that in many applications the subject and associated EEG sensor 10 may be remote from the apparatus to be controlled. Thus, isolator 18 may be replaced by any type of remote data link, such as a radio data link formed by a transmitter adjacent the EEG sensor 10 and an associated receiver at the site of the command decoder 12.

The pulses representative of the EEG signals from isolator 18 are applied to a pulse generator 20 which preferably reproduces uniform pulse or square waves signals compatible with the downstream logic circuitry in response to the applied pulse signals, which may have deteriorated due to transmission losses in the isolator or data link 18. Pulse generator 20 functions to enhance the accuracy and reliability of the command decoder 12 by rendering the operation of the downstream logic circuitry substantially independent of the quality of the upstream pulse signals. To this end, pulse generator 20 preferably comprises a conventional monostable multivibrator circuit.

The signal from pulse generator 20 is applied to a counter/decoder circuit 22 adapted to detect and differentiate the various encoded commands in accordance with the preferred encoding system. Since each command corresponds to a sequence of alpha waves of a different number, and each pulse from pulse generator 20 corresponds to an alpha wave, counter/decoder 22 in essence, merely comprises a counter for counting the pulses from pulse generator 20, the total thereof corresponding to the particular command. Of course, counter/decoder 22 preferably includes additional timing circuitry to detect the end of the sequence of alpha waves, corresponding to the completed transmission of the commands thereto. Moreover, such timing circuitry preferably requires the alpha waves to be received within a specified time interval, to render the apparatus unresponsive to randomly occurring alpha signals which will be involuntarily produced by the subject. The outputs of counter/decoder 22 are connected to switching circuitry 23, adapted to energize apparatus to accomplish the decoded commands.

Referring now to FIG. 3, counter/decoder 22 will now be described in greater detail. As briefly referred to hereinbefore counter/decoder 22 essentially comprises a counter for accumulating the pulses from pulse generator 20, the total thereof corresponding to the particular encoded command. In accordance with the preferred embodiment, applicants have found it most convenient to accomplish this counting in a BCD logic system and thereafter convert from BCD to decimal. Thus, counter/decoder 22 preferably comprises a BCD counter 26 which receives and counts the pulses from pulse generator 20. The output of BCD counter 26 is connected to a BCD latch or register which functions to store the total from counter 26 upon completion of a sequence of alpha waves. The output of latch circuit 28 thus comprises a BCD representation of the total number of alpha waves of a particular sequence or command. Latch 28 is connected to a decoder 30 which functions to convert the BCD representation of the command into a more usable form. Specifically, in BCD format, the command is represented by BCD signals on multiple leads. It is desired that each BCD command be represented by a signal on a single lead. Thus, decoder 30 preferably comprises a BCD to decimal decoder which converts the multi-lead BCD signals into a single signal on one of ten decimal leads. These decimal leads may thus be directly connected to the various acutators 14 associated with the particular commands.

As briefly referred to hereinbefore, counter/decoder 22 also includes timing circuitry in accordance with the preferred embodiment of the present invention. Specifically, in order to render the apparatus unresponsive to randomly occurring alpha signals which will be involuntarily produced by the subject, timing circuitry is provided which requires the alpha waves for a command to be received within a specified time interval in order to be counted. Specifically, there is provided a timer circuit 24 reset by the pulses from pulse generator 20. Timer 24 produces two output signals respectively applied to the reset input of counter 26 and to the control input of latch circuit 28. These two signals correspond to two different time intervals. Specifically, the signal from timer 24 to latch 28 defines the maximum time interval between successive alpha waves. In other words, if a pulse from pulse generator 20 is not followed in this time interval by another pulse, the total in counter 26 is transferred to the output of latch 28. This may be more readily understood by reference to FIG. 4 which graphically depicts the various timing signals involved in the illustrated counting of a four pulse sequence. Thus, the pulse generator 20 signal depicted comprises a sequence of four pulses counted by counter 26. Each of these pulses resets the timer 24. After the fourth pulse, no subsequent pulse is received within the specified time interval so that timer 24 produces a first pulse to latch 28. This pulse activates the latch 28 causing it to register the counter output in BCD. This BCD signal is then decoded into decimal by decoder 30 and applied to the appropriate actuator 14.

Of course, it is necessary to reset counter 26 after an encoded command has been counted and decoded. Thus, as briefly referred to hereinbefore, timer 24 produces a second signal applied to the reset input of counter 26. However, counter 26 must not be reset until its total has been entered in latch 28. Thus, the reset signal from timer 24 to counter 26 must be subsequent to the latching signal from timer 24 to latch 28. This is accomplished by including in timer 24 circuitry to produce the counter reset signal delayed from the latching signal. Thus, there is illustrated in FIG. 4 a reset pulse from timer 24 to counter 26 occurring after the latching pulse from timer 24 to latch 28. This signal resets counter 26 to zero and thus resets the counter/decoder 22 so that the command decoder is again ready for receipt of another encoded command.

The counter/decoder circuit 22, depicted in FIG. 3, may be conveniently constructed from readily available integrated circuits. Thus, counter 26 may comprise a type 7490 BCD counter. Latch circuit 28 may comprise a type 7475 4 bit latch while decoder circuit 30 may comprise a type 7441 BCD to decimal decoder.

Timer circuit 24 may comprise a multivibrator tiggered by the first pulse of a command. Since the desired time interval to be timed comprises approximately 0.2 seconds, it is convenient to operate the multivibrator at a greater frequency, and employ a counter to divide down the pulses therefrom to determine the preferred time interval. Thus, the signal from pulse generator 20 need merely be applied to the reset input of this timer counter to accomplish the desired resetting of the timer in response to the receipt of an alpha pulse signal. The output of timer 24 to the latch 28 and the delayed output to the reset input of counter 26 may merely be taken from the different outputs of the timer counter. For example, the latching signal from timer 24 to latch 28 may comprise the 6 output of the counter while the reset signal from timer 24 to counter 26 may comprise the 8 output of the counter. In this arrangement, the period of the multivibrator should be 1/6 of the desired time interval, or 1/30 seconds.

The operation of the EEG activated control system of the present invention may be better understood with reference to the following exemplary description of the generation and decoding of a command corresponding to a sequence of four alpha waves. Once the subject has placed the electrodes of the EEG sensor 10 on his head in a conventional manner, the command is produced by the subject voluntarily producing a burst of alpha activity containing four alpha waves. If fewer than four waves are accidentally produced, another burst can be produced within the time interval to make up the deficit. In accordance with the preferred embodiment this interval is 0.2 seconds. Thus, any correcting alpha burst must be produced within 0.2 seconds of the previous alpha burst.

The alpha waves thus produced are detected by EEG sensor 10 which produces corresponding pulse signals which are applied to the command decoder 12. These signals are transmitted via the isolator or data link 18 to pulse generator 20, causing pulse generator 20 to produce corresponding output pulses. Each of the pulses from pulse generator 20 causes timer 24 to reset and is additionally counted by counter 26. After the last pulse of the sequence, the fourth pulse of the described example, counter 24 is not reset due to the absence of a subsequent pulse and thus produces a latching signal causing the total in counter 26, namely, BCD four, to be entered in latch 28. The BCD output of latch 28 is decoded by decoder 30 into a decimal 4 signal which thus energizes the actuator 14 connected to the 4 decimal output lead of decoder 30, to accomplish the desired result.

In addition, the output of command decoder 12 may be displayed on display 16. Specifically, the BCD output of latch 28 may be applied to a BCD to seven segment numeric display. The numeric display 16 enables the subject to readily determine that the command has been correctly encoded, detected and decoded.

Since no subsequent alpha waves are produced, timer 24 continues to operate and thus produces a reset signal applied to the reset input of counter 26. This signal resets the circuitry enabling the processing of subsequent encoded commands.

The voluntary generation of short bursts of specific numbers of alpha waves is a skill which must, of course, be acquired by the subject. Preliminarily, the subject must learn to voluntarily produce alpha waves or in other words to enter the alpha state. This may be achieved readily through the conventional use of EEG bio-feedback training. Thereafter, the training required to practice the present invention departs from that conventionally employed in bio-feedback, wherein the emphasis is upon maintaining the alpha state for prolonged periods. In accordance with the present invention, the subject next learns to produce an almost instantaneous initiation of alpha waves. This can be accomplished by the subject repeatedly practicing the generation of a tone from an alpha bio-feedback machine, concentrating upon reducing the time required to produce the tone. After one has become proficient at producing the immediate initiation of alpha waves, the apparatus of the present invention may be employed in the remaining training. Specifically, the actuators 14 may be disconnected or otherwise rendered inoperative, and the subject may attempt to encode random numbers, while observing the results on the display 16. While initially the subject's accuracy may be quite low, practice will result in improvements approaching 100% accuracy. When suitable accuracy is obtained, the acutators 14 may be connected and energized, and the subject may thereafter practice the specific command selected for the operation of the apparatus to be controlled.

While a particular embodiment of the present invention has been depicted and described in detail, it is apparent that adaptations and modifications may occur to those skilled in the art. Specifically, the encoding and decoding technique described herein, while particularly convenient due to the substantial independence on the amplitude and frequency of the alpha waves, it is not essential to the realization of the present invention. Specifically, it is possible that other encoding techniques may be learned, such amplitude modulation or frequency modulation, and such encoding techniques may be employed with compatible decoding circuitry. Moreover, while alpha waves are employed in accordance with the preferred embodiment, other frequency ranges of EEG activity may be alternatively employed. It is to be expressly understood that these and other adaptations and modifications of the present invention may be employed without departing from the spirit and scope of the present invention, as set forth in the claims.

What is claimed is:

1. An electroencephalographic acutated control system responsive to a plurality of different commands voluntarily encoded on EEG signals in a predetermined serial digital encoding system wherein each command corresponds to a different predetermined number of waves voluntarily generated in a predetermined frequency range of electroencephalographic activity comprising: EEG sensor means for detecting EEG signals including at least the signals comprising said encoded commands, filter means for selecting signals within said predetermined frequency range from the detected EEG signals, command decoder means responsive to the filtered EEG signals for decoding each of said plurality of different commands including counter means for counting the number of waves of said filtered EEG signals to generate digital signals representative of the number of waves of and corresponding to a digital representation of the encoded command and actuator means responsive to said digital signals of said counter means for controlling apparatus adapted to accomplish each of said commands in response thereto.

2. Apparatus according to claim 1 wherein said predetermined frequency range comprises alpha waves from about 7.5 Hz to about 13 Hz.

3. Apparatus according to claim 1 comprising display means responsive to said command decoder means for displaying a numeric representation of the command decoded by said command decoder means.

4. Apparatus according to claim 3 wherein said display means comprises a seven segment numeric display.

5. Apparatus according to claim 1 wherein said actuator means comprises switching circuitry for energizing apparatus adapted to accomplish said commands.

6. Apparatus according to claim 1 wherein said command decoder means comprises pulse generator means for regenerating pulses corresponding to the pulse from said EEG sensor means.

7. Apparatus according to claim 1 wherein said counter means comprises a binary coded decimal counter.

8. Apparatus according to claim 7 wherein said command decoder means comprises latch means for temporarily storing the total in said counter upon cessation of a sequence of waves of the EEG signals.

9. Apparatus according to claim 8 wherein said command decoder means comprises decoder means for converting the binary coded decimal representation of said commands from said latch means to signals on an array of leads respectively connected to the corresponding actuator means.

10. Apparatus according to claim 1 wherein said command decoder means comprises timer means for conditioning said command decoder means to respond only to subsequent pulses received within a specified time interval from the previous of said pulses.

11. Apparatus according to claim 10 wherein said timer means comprises an interval timer having a time interval corresponding to said specified time interval and means for resetting said interval timer in response to receipt of a pulse from said pulse generator means.

12. Apparatus according to claim 11 wherein said time interval is about 0.2 seconds.

13. Apparatus according to claim 1 comprising amplifier means for amplifying the detected EEG signals from said sensor means for applying the amplified EEG signals to said filter means.

14. Apparatus according to claim 13 comprising pulse forming means responsive to the filtered EEG signals for generating pulses coresponding to each of the waves of said filtered EEG signals, said pulses being applied to the counter means of said command decoder means.

15. A method for controlling apparatus in response to electroencephalographic signals comprising voluntarily encoding at least one of a plurality of commands on EEG signals in a predetermined serial digital encoding system wherein each command corresponds to a different predetermined number of waves voluntarily generated in a predetermined frequency range of electroencephalographic activity, detecting said EEG signals including at least the signals comprising said encoded commands, decoding said commands from the detected EEG signals within said predetermined frequency range, decoding said commands from the detected EEG signals by counting the number of waves of said EEG signals within said predetermined frequency range to form a digital representation of number of waves of and corresponding to a digital representation of the encoded command and controlling said apparatus in response to said digital representation of the encoded command.

16. The method according to claim 15 wherein said predetermined frequency range comprises alpha waves from about 7.5 Hz to about 13 Hz.

17. The method according to claim 16 comprising filtering said alpha waves from the detected EEG signals.

18. The method according to claim 15 wherein the step of counting comprises counting only waves detected within a specified time interval from the previous wave.

* * * * *